United States Patent [19]

Marrelli

[11] Patent Number: 5,140,271
[45] Date of Patent: Aug. 18, 1992

[54] WATERCUT MEANS AND METHOD WITH DEBRIS REDUCING TEST CELL

[75] Inventor: John D. Marrelli, Houston, Tex.

[73] Assignee: Texaco Inc., White Plains, N.Y.

[21] Appl. No.: 457,212

[22] Filed: Dec. 26, 1989

[51] Int. Cl.$^5$ ............................................. G01N 22/00
[52] U.S. Cl. .................................... 324/640; 73/61.43; 73/61.63
[58] Field of Search ...................... 324/640, 639, 71.4, 324/446, 450, 204, 324, 376; 73/61.1 R, 61.4, 61 R; 333/248, 257

[56] References Cited

U.S. PATENT DOCUMENTS

| | | | |
|---|---|---|---|
| 2,895,102 | 7/1959 | Hart et al. | 324/450 |
| 3,617,868 | 11/1971 | Beitel et al. | 324/326 |
| 4,137,494 | 1/1979 | Malley et al. | 324/450 |
| 4,240,028 | 12/1980 | Davis, Jr. | 324/61 R |
| 4,434,398 | 2/1984 | Berg et al. | 324/71.4 |
| 4,499,418 | 2/1985 | Helms et al. | 73/61.1 R |
| 4,651,085 | 3/1987 | Sakurai et al. | 324/639 |
| 4,774,680 | 9/1988 | Agar | 364/550 |
| 4,881,412 | 11/1989 | Northedge | 73/861.04 |
| 4,902,961 | 2/1990 | De et al. | 324/640 |

Primary Examiner—Walter E. Snow
Assistant Examiner—Maura K. Regan
Attorney, Agent, or Firm—Robert A. Kulason; James J. O'Loughlin; Ronald G. Gillespie

[57] ABSTRACT

A petroleum stream microwave watercut monitor of the present invention includes a test cell having a petroleum flowing through it. A source, connected to a first antenna located within the test cell, provides microwave energy to the first antenna so as to irradiate the petroleum stream in the test cell with microwave energy. A second antenna located in the test cell and connected to a detector outside of the test cell receives the microwave energy that has passed through the petroleum stream and provides it to the detector. The detector provides an intensity signal corresponding to the received microwave energy. An indicator provides an indication of the watercut of the petroleum stream in accordance with the intensity and the phases difference between the microwave energy provided by the source and the received microwave energy. The test cell means also includes means for reducing an amount of debris in a portion of the petroleum stream flowing between both antenna.

18 Claims, 2 Drawing Sheets

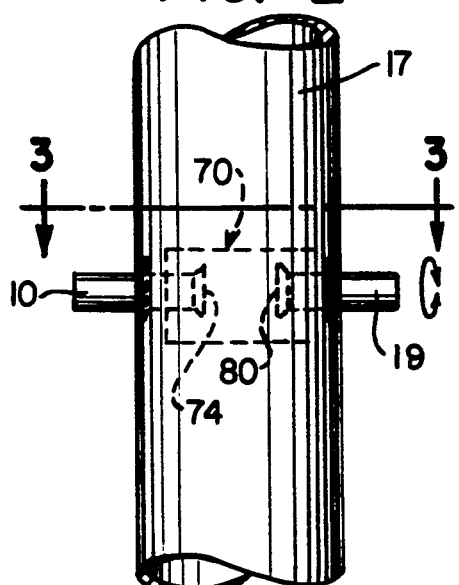
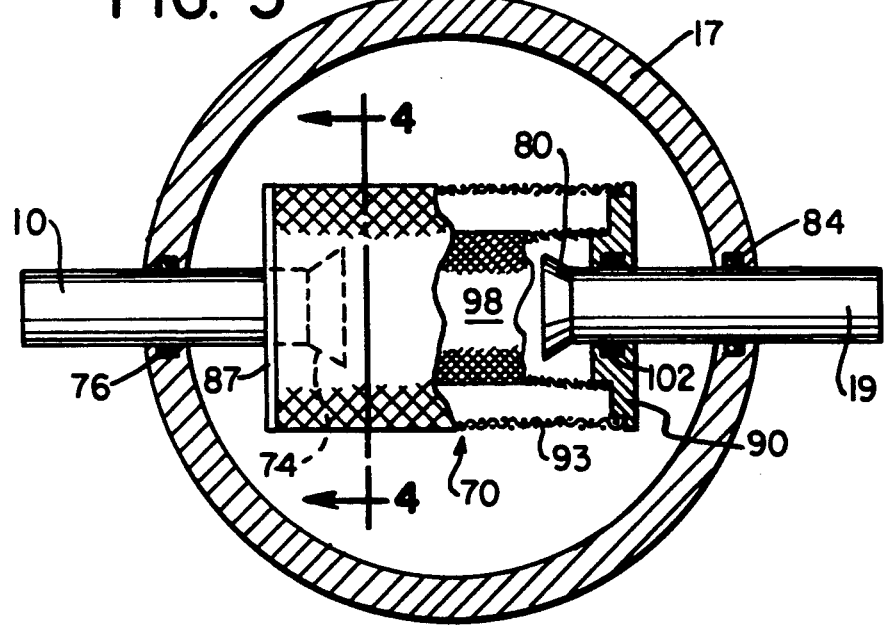
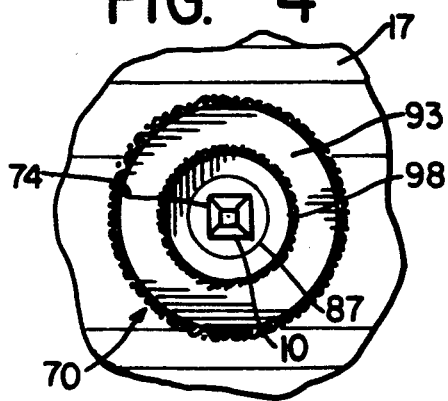

WATERCUT MEANS AND METHOD WITH DEBRIS REDUCING TEST CELL

BACKGROUND OF THE INVENTION

1. Field of the Invention

The present invention is a watercut means and method in general, and more particular, a microwave watercut means and method.

2. Summary of the Invention

A petroleum stream microwave watercut monitor of the present invention includes a test cell having a petroleum flowing through it. A source, connected to a first antenna located within the test cell, provides microwave energy to the first antenna so as to irradiate the petroleum stream in the test cell with microwave energy. A second antenna located in the test cell and connected to a detector outside of the test cell receives the microwave energy that has passed through the petroleum stream and provides it to the detector. The detector provides an intensity signal corresponding to the received microwave energy. An indicator provides an indication of the watercut of the petroleum stream in accordance with the intensity and the phases difference between the microwave energy provided by the source and the received microwave energy. The test cell means also includes means for reducing an amount of debris in a portion of the petroleum stream flowing between both antenna.

The objects and advantages of the invention will appear more fully hereinafter, from a consideration of the detailed description which follows, taken together with the accompanying drawings wherein one embodiment is illustrated by way of example. It is to be expressly understood, however, that the drawings are for illustrative purposes only and are not to be construed as defining the limits of the invention.

DESCRIPTION OF THE DRAWINGS

FIG. 2 is a representation of the test cell shown in FIG. 1.

FIG. 3 is a detailed representation of the test cell shown in FIG. 1.

FIG. 4 is a cross sectional view along the lines for 4 of the test cage shown in FIG. 3.

DESCRIPTION OF THE INVENTION

Figure 1:
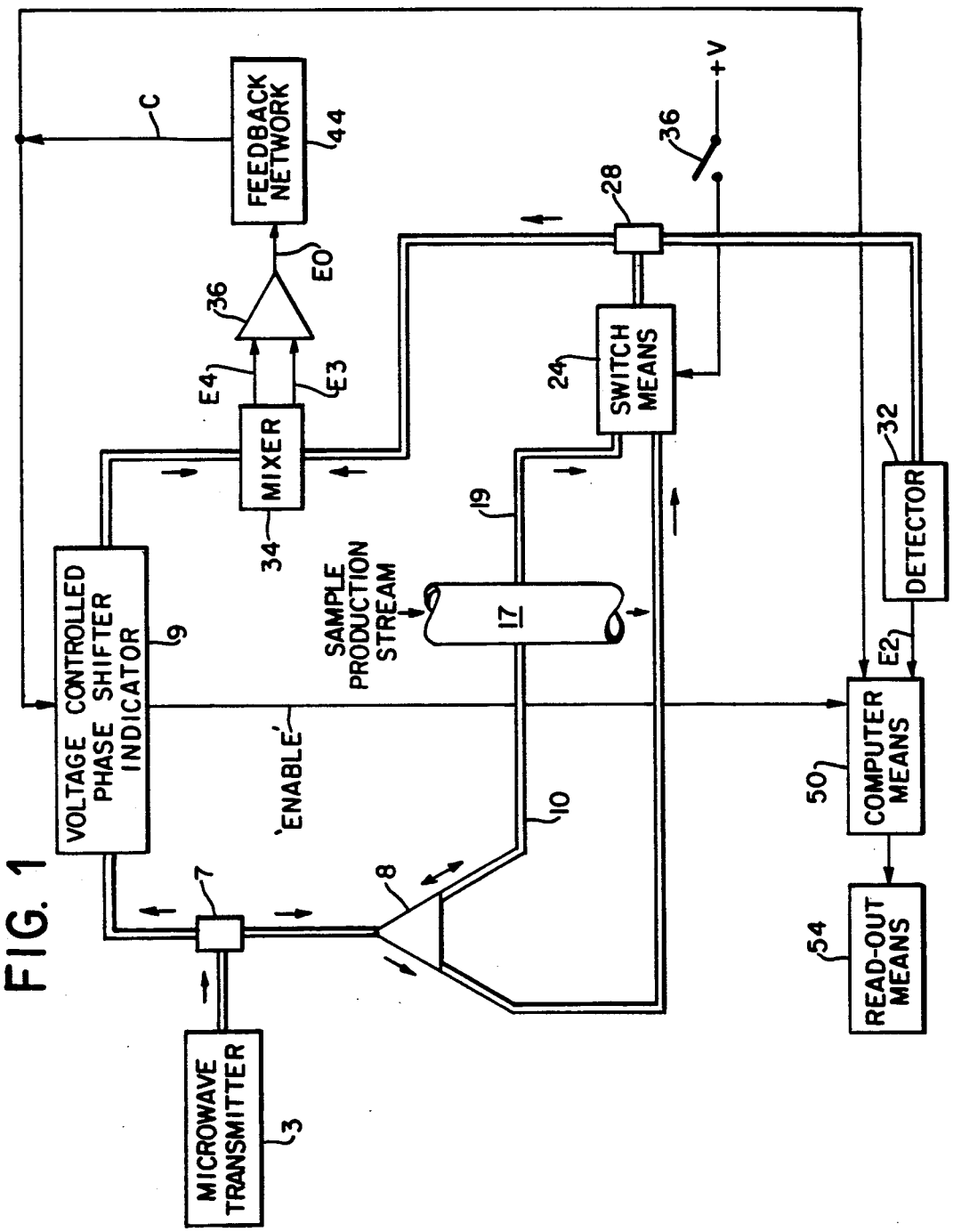
FIG. 1 is a simplified block diagram of a microwave watercut monitor constructed in accordance with the present invention.

The watercut monitor shown in FIG. 1 includes a microwave transmitter 3 providing electromagnetic energy, hereinafter referred to as microwave energy, at a microwave frequency. Transmitter 3 is low powered and may use a microwave gun source. Transmitter 3 provides microwave energy to directional coupler 4. Directional coupler 4 provides microwave energy to a conventional type voltage controlled phase shifter 9 and to a circulator 8. All conductance or carrying of microwave energy is accomplished by using conventional type waveguides.

Circulator 8 provides microwave energy via a waveguide 10, to a petroleum stream passing through a test cell 17. Test cell 17 will be described in greater detail hereinafter. The microwave energy that passes through the petroleum stream is provided by way of a waveguide 19 to a switch means 24 which when in one state provides received microwave energy as test microwave energy to a directional coupler 28. Directional coupler 28 provides the test microwave energy to a detector 32 and to a mixer 34. Detector 32 provides a signal E2 corresponding to the intensity of the test microwave energy.

The petroleum stream may also reflect some of the microwave energy back which passes back to circulator 8 by way of waveguide 10. Circulator 8 blocks the reflected microwave energy from feeding back to transmitter 3 and provides the reflected microwave energy which becomes more important as the distance across test cell 17 increases. This is especially true where test cell 17 is used with a large pipeline carrying the petroleum stream.

A positive direct current voltage $+V$ is provided to switch means 24. With switch means 24 in another state, switch means 24 provides the reflected microwave energy from circulator 8 as the test microwave energy.

The microwave energy from voltage control phase shifter 9, hereinafter called the reference microwave energy, and the test microwave energy from directional coupler 28, are provided to mixer 34 which mixes them to provide two electrical signals E3, E4, representative of the phases of the reference microwave energy and the test microwave energy, respectively.

A differential amplifier 36 provides an output signal EO in accordance with the difference between the signals E3, E4 and hence the phase difference between the test microwave energy and the reference microwave energy. Signal EO, and hence the signal C, decreases in amplitude until there is substantially 90° phase difference between the reference microwave energy and the test microwave energy. Voltage control phase shifter 9 indicates the amount of phase shift required to eliminate the phase difference and provides an "enable" signal to computer means 50.

Signals E2 and C are provided to computer means 50 which contains within its memory means data related to phase and amplitude for various percentages of watercuts that could be encountered in the production stream. The "enable" signal, provided by phase shifter 9 to computer means 50, allows computer means 50 to utilize signals C and E1 to select the proper watercut value. Computer means 50 provides signals, corresponding to the selected watercut value, to readout means 54 which may be either digital display means or recording means or a combination of two.

With reference to FIGS. 2, 3, and 4, waveguide 10 enters test call 17 and a test cage 70 and is connected to an antenna 74. A seal 76 prevents any of the petroleum stream in test cell 17 from leaking out. Similarly waveguide 19 enters test cell. 17 and test cage 70 is connected to an antenna 80. A seal 84 prevents the petroleum stream from leaking from test cell 17.

As shown in FIGS. 1 and 2, microwave energy from circulator 8 will pass through line 10 and is radiated by antenna 74 to antenna 80. Antenna 80 receives microwave energy and provides the received microwave through waveguide 19. Cage 70 is a self cleaning device that allows a fluid mixture to flow between antennas 74 and 80 while removing particles and debris that might be in the petroleum stream.

Test cage 70 has two end pieces 87 and 90 designed to support a coarse wire mesh 93 as an outside screen and a fine wire mesh 98 as an inner screen. The passage of waveguides 10 and 19 through end plates 87 and 90, respectively, is supported by a ball bearing system 102.

Test cage 70 will rotate around waveguides 10 and 19 in response to the flow of the petroleum stream.

In operation, as debris in the petroleum stream comes in contact with cage 70, the larger elements of the debris makes contact with the coarse wire mesh 93 and fall to the bottom of the test cell 17 and is carried away by the flow of the petroleum stream. Smaller elements of the debris may enter cage 70 but they will come in contact with fine wire mesh 98 and be stopped from entering that portion of test cage 70 that lies between antennas 74 and 80. The debris stop by fine wire mesh 98 may be carried by fine wire mesh 98 and fall away under the influences of gravity and due to the rotation of cage 70. The fallen smaller elements will pass out of cage 70 due to the flow of the petroleum stream so that there is not a build up of debris in the vicinity of the microwave energy path between antennas 74 and 80.

The present invention as hereinbefore described is a microwave watercut monitor with apparatus for reducing the amount of debris in a petroleum stream passing between microwave antennas so as to enhance the accuracy of the watercut monitor.

What is claimed is:

1. A petroleum stream microwave watercut monitor comprising:

test cell means for having a petroleum stream flowing through it, source means for providing microwave energy, first antenna means connected to the source means for irradiating the petroleum stream flowing in the test cell means with microwave energy, second antenna means for receiving microwave energy that has passed through the petroleum stream, detector means connected to the second antenna means for detecting the intensity of the received microwave energy and providing an intensity signal corresponding thereto, and indicator means connected to the second antenna means, to the source means and to the detector means for providing an indication of the watercut of the petroleum stream in accordance with the intensity signal and the phase difference between the microwave energy from the source means and the received microwave energy; and in which said test cell means includes means spatially arranged with both antenna means for reducing an amount of debris in a portion of the petroleum stream flowing between both antenna means.

2. A monitor as described in claim 1 in which
the first antenna means includes:
a first antenna located in the test cell means, and
first waveguide means connected to the first antenna and to the source means for providing the microwave energy from the source means to the first antenna so as to cause the first antenna to irradiate the petroleum stream with microwave energy;
the second antenna means includes:
a second antenna located in the test cell means and spatially arranged with the first antenna, which receives microwave energy from the petroleum stream, and
second waveguide means connected to the second antenna and to the detector means for providing the microwave energy received by the second antenna to detector means; and
the test cell means includes:
sealing means for sealing the test cell means where the first waveguide means and the second waveguide means enter and exit the test cell means, respectively, so that test cell means does not leak.

3. A monitor as described in claim 2 further comprises:
attaching means for attaching the reducing means to the first and second waveguide means in a manner so that both antennas are located within the reducing means.

4. A monitor as described in claim 3 in which the reducing means is of a construction so as to allow the petroleum to flow through the reducing means while the reducing means removes debris from that portion of the petroleum stream flowing through the reducing means.

5. A monitor as described in claim 4 in which the reducing means includes:
first screen means for preventing the debris of a first predetermined size or greater from entering the reducing means.

6. A monitor as described in claim 5 in which the reducing means further includes:
second screen means for preventing debris of a second predetermined size or greater from passing between the two antennas.

7. A monitor described in claim 6 in which the second predetermined size is smaller than the first predetermined size and the second screen means is located closer to the antennas than the first screen means.

8. A monitor as described in claim 7 in which the reducing means is cylindrical in shape and the first screen means has a diameter greater than the diameter of the second screen means; and the reducing means further comprising two end piece means for holding the first and second screen means in spatial relationship to both antennas.

9. A monitor as described in claim 8 in which each attaching means includes:
a ball bearing assembly mounted in a different end piece means so to allow the reducing means to rotate in response to the petroleum stream flow.

10. A petroleum stream microwave watercut monitoring method comprising the steps of:
flowing a petroleum stream through a test cell,
providing microwave energy from a source,
irradiating the petroleum stream flowing in the test cell means with the microwave energy from the source,
receiving microwave energy that has passed through the petroleum stream,
detecting the intensity of the received microwave energy with a detector,
providing an intensity signal corresponding to the detected microwave energy, and
providing an indication of the watercut of the petroleum stream in accordance with the intensity signal and the phase difference between the microwave energy from the source and the received microwave energy; and
in which the flowing step includes reducing an amount of debris in a portion of the petroleum stream passing between where the petroleum stream is irradiated with microwave energy and where the microwave energy is received, with reducing means.

11. A method as described in claim 10 in which
the irradiating step includes:
locating a first antenna in the test cell; and providing the microwave energy from the source to the first antenna with a first waveguide so as to cause the first antenna to irradiate the petroleum stream with microwave energy, the receiving step includes:

locating a second antenna in the test cell and spatially arranged with the first antenna; and receiving microwave energy from the petroleum stream with the second antenna; and providing the microwave energy received by the second antenna to the detector by way of a second waveguide; and further comprising:

sealing the test cell where the first waveguide and the second waveguide enter and exit the test cell, respectively, so that the test cell does not leak.

12. A method as described in claim 11 further comprising:

attaching the reducing means to the first and second waveguide in a manner so that both antennas are located within the reducing means.

13. A method as described in claim 12 in which the reducing step includes allowing a portion of the petroleum stream to flow through the reducing means while the reducing means removes debris from that portion of the petroleum stream flowing through the reducing means.

14. A method as described in claim 13 in which the reducing step includes:

preventing the debris of a first predetermined size or greater from entering the reducing means with first screen means.

15. A method as described in claim 14 in which the reducing step further includes:

preventing debris of a second predetermined size or greater from passing between the two antennas with second screen means.

16. A method described in claim 15 in which:

the second predetermined size is smaller than the first predetermined size, and further comprising the step of:

locating the second screen means closer to the antennas than the first screen means.

17. A method as described in claim 16 in which the reducing step further comprises the step of holding the first and second screen means in spatial relationship to both antennas with end pieces.

18. A method as described in claim 17 in which the attaching step includes:

mounting a ball bearing assembly in each end piece so as to allow the reducing means to rotate in response to the petroleum stream flow.

* * * * *